(12) United States Patent
Kwon et al.

(10) Patent No.: US 8,296,300 B2
(45) Date of Patent: Oct. 23, 2012

(54) METHOD FOR RECONSTRUCTING PROTEIN DATABASE AND A METHOD FOR SCREENING PROTEINS BY USING THE SAME METHOD

(75) Inventors: Kyung-Hoon Kwon, Daejeon (KR); Jong Shin Yoo, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 725 days.

(21) Appl. No.: 12/373,495

(22) PCT Filed: Aug. 18, 2006

(86) PCT No.: PCT/KR2006/003261
§ 371 (c)(1),
(2), (4) Date: Jan. 12, 2009

(87) PCT Pub. No.: WO2008/007821
PCT Pub. Date: Jan. 17, 2008

(65) Prior Publication Data
US 2009/0319558 A1  Dec. 24, 2009

(30) Foreign Application Priority Data

Jul. 12, 2006 (KR) .................. 10-2006-0065533

(51) Int. Cl.
*G06F 7/00* (2006.01)
(52) U.S. Cl. .............. 707/737; 702/19; 702/23; 702/27; 703/2; 706/13; 707/708; 707/722; 707/771; 707/776; 707/802
(58) Field of Classification Search .................. None
See application file for complete search history.

(56) References Cited

U.S. PATENT DOCUMENTS

| 6,512,981 B1 | 1/2003 | Eisenberg et al. | |
|---|---|---|---|
| 2004/0204861 A1* | 10/2004 | Benner | 702/19 |
| 2008/0234945 A1* | 9/2008 | Walk et al. | 702/19 |

FOREIGN PATENT DOCUMENTS

| KR | 10-2005-0064644 | 6/2005 |
|---|---|---|
| WO | WO 01/67299 | 9/2001 |
| WO | WO 03/019417 | 3/2003 |
| WO | WO 03/038728 | 5/2003 |

OTHER PUBLICATIONS

Alm et al., "Detection and Identification of Protein Isoforms Using Cluster Analysis of MALDI-MS Mass Spectra", 2006, Journal of Proteome Research, vol. 5, pp. 785-792.*
Duncan et al., "Parallel Tandem: A Program for Parallel Processing of Tandem Mass Spectra Using PVM or MPI and X!Tandem", 2005, Journal of Proteome Research, vol. 4, pp. 1842-1847.*
Samuelsson et al., "Modular, scriptable and automated analysis tools for high-throughput peptide mass fingerprinting", 2004, Bioinformatics, vol. 20, No. 18, pp. 3628-3635.*

* cited by examiner

*Primary Examiner* — Carolyn L. Smith
(74) *Attorney, Agent, or Firm* — Greenlee Sullivan P.C.

(57) ABSTRACT

The present invention relates to a method for reconstructing protein database for identifying a protein and a method for screening a protein using the same, more precisely a method for reconstructing protein database, and a method for identifying a protein using the same. The method for reconstructing protein database and the method for identifying the protein of the invention are very useful for the investigation of endogenous proteins and their functions and interactions, and are further effectively used for the development of diagnostic and therapeutic agents for various diseases.

18 Claims, 3 Drawing Sheets

METHOD FOR RECONSTRUCTING PROTEIN DATABASE AND A METHOD FOR SCREENING PROTEINS BY USING THE SAME METHOD

CROSS-REFERENCE TO RELATED APPLICATIONS

This application is the U.S. National Stage of International Application No. PCT/KR2006/003261, filed Aug. 18, 2006, which claims the benefit of Korean Patent Application KR10-2006-0065533, filed Jul. 12, 2006, both of which are hereby incorporated by reference to the extent not inconsistent with the disclosure herewith.

TECHNICAL FIELD

The present invention relates to a method for reconstructing protein database for protein identification and a method for identifying a protein using the same, more precisely a method for reconstructing the old protein database for more efficient protein identification and a method for identifying a protein by applying the mass spectra of the proteins or peptides measured by mass spectrometer to the reconstructed protein database by using the same.

BACKGROUND ART

Mass spectrometry is a very important assay method for biopolymer, which can be further linked to protein database searching and thus be a crucial assay in proteomics study. The conventional methods for searching a protein by using a mass spectrum have been using softwares such as SEQUEST (Eng et al., *J. Am. Soc. Mass Spectrom.* 5:976-989, 1994; Thermo Electron Corp., USA), Mascot (Perkins et al., *Electrophoresis,* 20:3551-3567, 1999; Matrix Science Ltd., USA, www<dot>matrixscience<dot>com , Sonar (Field, H. I. et al., *Proteomics,* 2:36-47, 2002; bioinformatics<dot>genomicsolutions<dot>com/) and X!Tandem (Craig et al., *Bioinformatics,* 20:1466-1467, 2004; Proteome Software Inc., USA). According to the above methods, each target-to-be protein is extracted from a database comprising amino acid sequences and its mass spectrum pattern is predicted, which is then compared with the real mass spectrum investigated. The search algorithm used for the software for protein searching is exemplified by MOWSE algorithm (Pappin et al., *Curr. Biol.* 3:327-332, 1993), SEQUEST algorithm (Eng et al., *J. Am. Soc. Mass Spectrom.* 5:976-989, 1994), etc.

According to the fast accumulation of protein related information, the protein sequence database increases tremendously. So, if a database comprises all the sequences, searching efficiency decreases, so that it will be of no practical use. To overcome this problem, a more sophisticated sequence database such as UniProtKB/SwissProt (Bairoch et al., *Nucleic Acids Res.* 33:D154-159, 2005; www<dot>ebi<dot>uniprot<dot>orq/uniprot-srv/) or IPI database (Kersey et al., *Proteomics* 4(7):1985-1988, 2004; www<dot>ebi<dot>ac<dot>uk/IPI/IPIhelp<dot>html) can be used for database searching using a mass spectrum. These databases comprise the representative protein sequences with elimination of similar sequences which have been picked up from the known protein databases. They only contain 20% of the proteins listed in NCBI nr database of National Center for Biotechnology Information, USA, which is an integrated protein sequence database, so that they can be more effectively used for database searching using a mass spectrum.

Although these sophisticated sequence databases can make protein sequence searching easy and fast with the representative protein sequences, they might not be able to confirm some similar protein sequence. In using the general sequence searching program, a target sequence can be identified as long as there is a similar sequence in the database. However, mass spectrometry is a method to identify a peptide by investigating the molecular weight of the peptide. Therefore, if the difference between sequences is big, the screening result is controversial. So, to be practical, the size of a database has to be reduced, but for more accurate analysis, a database has to include various sequences. In particular, to find out some modifications on a specific region on a protein by using a molecular weight, the existence of the corresponding sequence in database is a critical factor for screening accuracy. Thus, an algorithm that is able to calculate similar sequence in mass spectrum has been proposed (Creasy et al., *Proteomics* 2(10):1426-34, 2002; Kayser et al., *J. Biomol. Tech.* 15(4):285-95, 2004). However, using this algorithm takes long time and the results might be in question.

DISCLOSURE

Technical Problem

It is an object of the present invention to provide a method for reconstructing the conventional protein database for more efficient protein identification and a method for identifying proteins or peptides by using the mass spectra to search out proteins or peptides from the reconstructed protein database.

Technical Solution

To describe the present invention in more detail, descriptions of the terms used herein are given as follows:

"Clustering" indicates a technique for grouping protein sequences of each individual database by taking various factors into consideration.

"Representative protein" indicates a representative of the group of proteins having at least 60% homology, selected from protein sequence database.

"Tandem mass spectrometry" is a method for mass analysis to separate parent ions and its subsequent mass analysis of the fragments of the parent ions.

To achieve the above object, the present invention provides a method for reconstructing protein database structure for protein search.

The present invention also provides a method for identifying a protein using the reconstructed protein database of the invention.

Hereinafter, the present invention is described in detail.

The present invention provides a method for reconstructing protein database comprising the following steps:

i) Grouping proteins having a required homology by using the clustering software from the primary database which minimizes the overlapping of proteins and then recording sequence information of each protein group on a recording system of a computer; and ii) Designating a representative protein in each protein group and then constructing a representative protein database composed of the representative proteins, followed by recording the results containing sequence information on a recording system of a computer.

The reconstructed representative protein database above is the database in minimum size for identification of a protein, making protein identification process fast.

The primary database above is preferably IPI database, UniprotKB/Swissprot database or nrdb90 database, but not always limited thereto. The above databases can be downloaded at the following internet addresses:

IPI: ftp<dot>ebi<dot>ac<dot>uk/pub/databases/IPI/current/

UniprotKB/Swissprot: ftp<dot>expasy<dot>org/databases/uniprot/

Nrdb90: ftp<dot>ebi<dot>ac<dot>uk/pub/databases/nrdb90/

The clustering software is preferably CD-HIT (bioinformatics<dot>org/cd-hit/, Li, W. et al., *Bioinformatics* 17:282-283, 2001; Li, W. et al, *Bioinformatics* 18:77-82, 2002), GeneRAGE (www<dot>ebi<dot>ac<dot>uk/research/, Enright, A.J. and Ouzounis, C.A., *Bioinformatics*, 16(5):451-457, 2000), TribeMCL (micans<dot>orq/mcl/src/, Enright, A.J. et al., *Nucleic Acids Res.* 30(7):1575-1584, 2002) or nrdb90 (Holm, L., Sander, C., *Bioinformatics*, 14:423-429, 1998), but not always limited thereto.

The required homology mentioned above is preferably 60%, 65%, 70%, 75%, 80%, 85%, 90% or 95%, and more preferably 60%, but not always limited thereto.

The method for reconstructing database of the present invention can additionally include the following steps:

iii) Screening tandem mass spectra of each sample obtained by mass spectrometer by using a software for sequence searching based on the conventional sequence searching algorithm with the representative protein database and then preparing the primary protein list comprising those proteins matched; and iv) Constructing the secondary database with those proteins of the groups of the above step i) which the proteins in the primary protein list belong to and then recording the sequence information on a recording system of a computer.

The secondary database above is smaller than the primary database but contains more sequence variation than the representative protein database. Thus, once a similar protein sequence to a target sequence is found in the representative protein database, the exact sequence can be identified by searching the secondary database.

The method for reconstructing protein database of the present invention can further include the following steps:

v) Screening tandem mass spectrum of each sample obtained by mass spectrometer by using a software for sequence searching based on the conventional sequence searching algorithm with the secondary protein database and then preparing the secondary protein list comprising those proteins matched; and vi) Selecting proteins related to the primary protein list made in the above step iii) from the third database containing a variety of protein sequences and then grouping them to construct the forth protein database, followed by recording the sequence information on a recording system of a computer.

The method for reconstructing protein database of the present invention can also include the following additional steps:

vii) Screening tandem mass spectrum of a specific sample obtained by mass spectrometer by using a software for sequence searching based on the conventional sequence searching algorithm with the forth protein database and then preparing the third protein list comprising those proteins matched;

viii) Screening tandem mass spectrum of a specific sample obtained by mass spectrometer by using a software for sequence searching based on the conventional sequence searching algorithm containing the modification conditions with the forth protein database and then preparing the forth protein list comprising the modified proteins matched; and ix) Preparing the list of identified proteins by taking all the lists from the primary to the forth protein lists into consideration, and printing the results by using an output unit of a computer.

As mentioned before, the third database includes a variety of sequences. The third database and the primary database, which is the representative database, are combined together, with which clustering software is executed. As a result, groups containing both the representative proteins and proteins of the third database are prepared. At this time, representative proteins have low homology with one another, so that they are grouped into different groups, and each group contains a representative protein and its similar proteins, resulting in the forth protein sequence database. In the meantime, the third database includes various sequences, so that some of them do not have homology with any representative protein. Therefore, groups not containing any representative protein can also be prepared. So, the numbers of the forth database groups can be more than those of representative proteins of the primary database.

To screen tandem mass spectra by using various searching methods including protein modification, the above representative protein database, the secondary database or the forth database are all available. However, the reconstructed forth database explained above is most preferred. The forth database which has been generated by the method for reconstructing protein database of the invention is characterized by smaller size than the third database of whole protein sequences without sacrificing the sequence diversity, in fact, rather keeping the maximum variety of protein sequences. Therefore, after screening a protein by using the primary, the secondary and the forth databases, more details of the obtained tandem mass spectrum can be screened by more detailed options such as protein modifications with the forth database, which takes shorter screening time, compared with when using the third database, and has less chance to miss a protein that is hard to identify with the primary database.

The sequence information of the above steps ii, iv and vi is formatted preferably by FASTA, but not always limited thereto.

In steps ii, iv and vi, various internal/external recording media can be used as a recording system of a computer, which is exemplified by HDD, FDD, CD-ROM, CD-R, CD-RW, DVD-ROM, DVD-RAM, DVD-RW±, MD (MiniDisk), MMC (MultiMedia Card), SMC (Smart Media Card), Flash-memory, SD (Secure Didital) card, CF (CompactFlash) card, MemoryStick, magnetic tape, etc, but not always limited thereto, and HDD is most preferred.

In steps iii and v, the software for sequence searching is SEQUEST (Eng et al., *J. Am. Soc. Mass Spectrom.* 5:976-989, 1994; Thermo Electron Corp., USA), Mascot (Perkins et al., *Electrophoresis,* 20:3551-3567, 1999; Matrix Science Ltd., USA, www.matrixscience.com), Sonar (Field, H. I. et al., *Proteomics,* 2:36-47, 2002; bioinformatics<dot>qenomicsolutions<dot>com/) or X!Tandem (Craig et al., *Bioinformatics,* 20:1466-1467, 2004; Proteome Software Inc., USA) but not always limited thereto.

The third database can be any database only if there are plenty of sequence information, but NCBI nr database, EST (Expressed Sequence Tag) database (www<dot>ncbi<dot>nlm<dot>nih<dot>gov/dbEST/), amino acid sequence database obtained from genome sequence are preferred. The third database can be utilized alone or together with other databases having various sequence information.

The database for screening is composed of the following three databases:

First is the representative protein database, which is the primary database that minimizes the overlapping of proteins. In this database, proteins are grouped according to the similarity and a representative protein is appointed for each group. The representative protein database is composed of those representative proteins, which is the primary database to be screened for the reconstructed hierarchical database of the present invention.

The secondary database is composed of those proteins selected from the primary database that exhibit the same characters as those proteins screened by using the representative protein database. The secondary database is smaller than the primary database but has larger variety of sequences that the representative protein database cannot provide.

Figure 1:
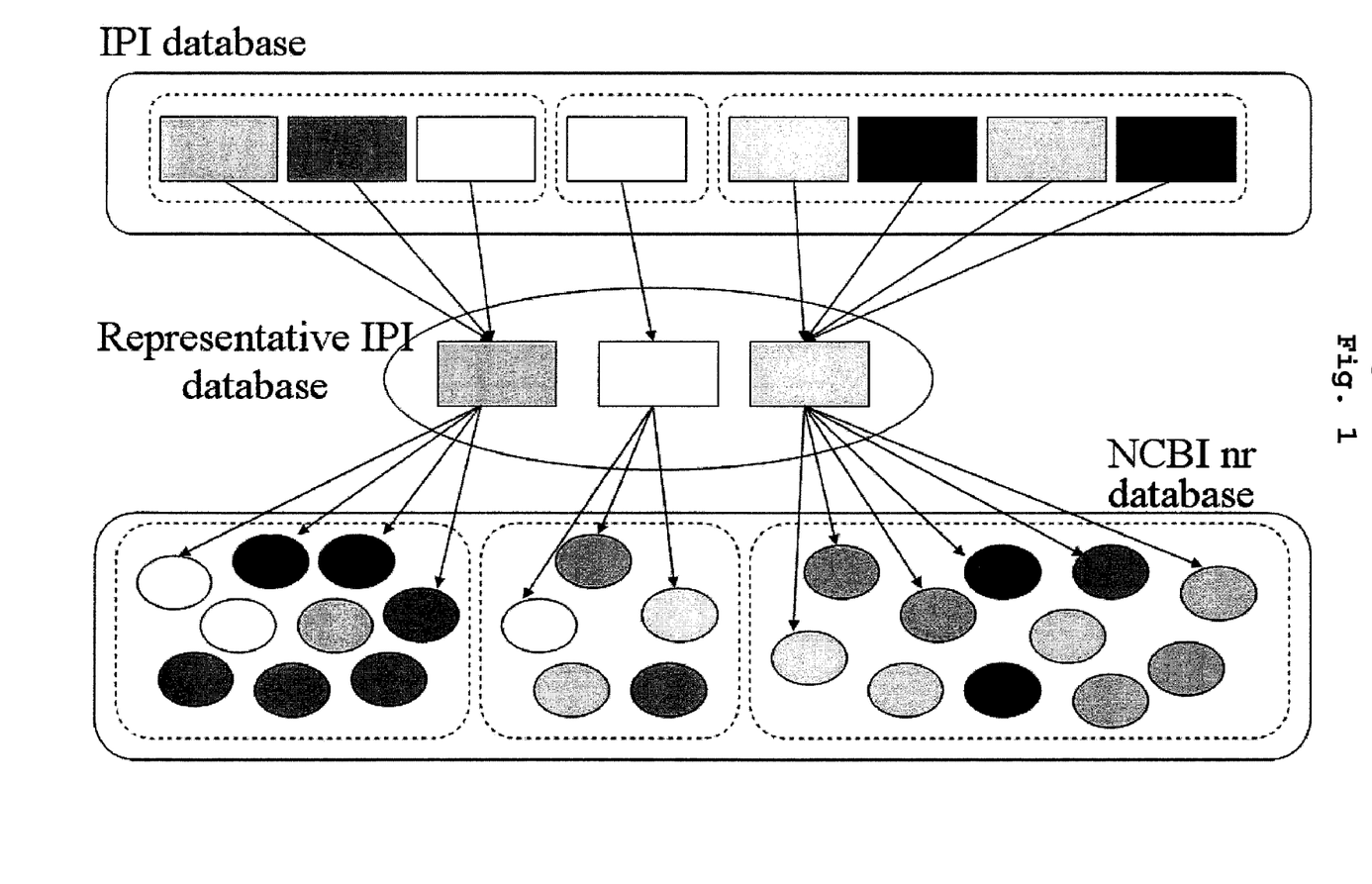
FIG. 1 is a schematic diagram illustrating the structure of the constructed database, based on the similarity between database A and database B.
Figure 2:
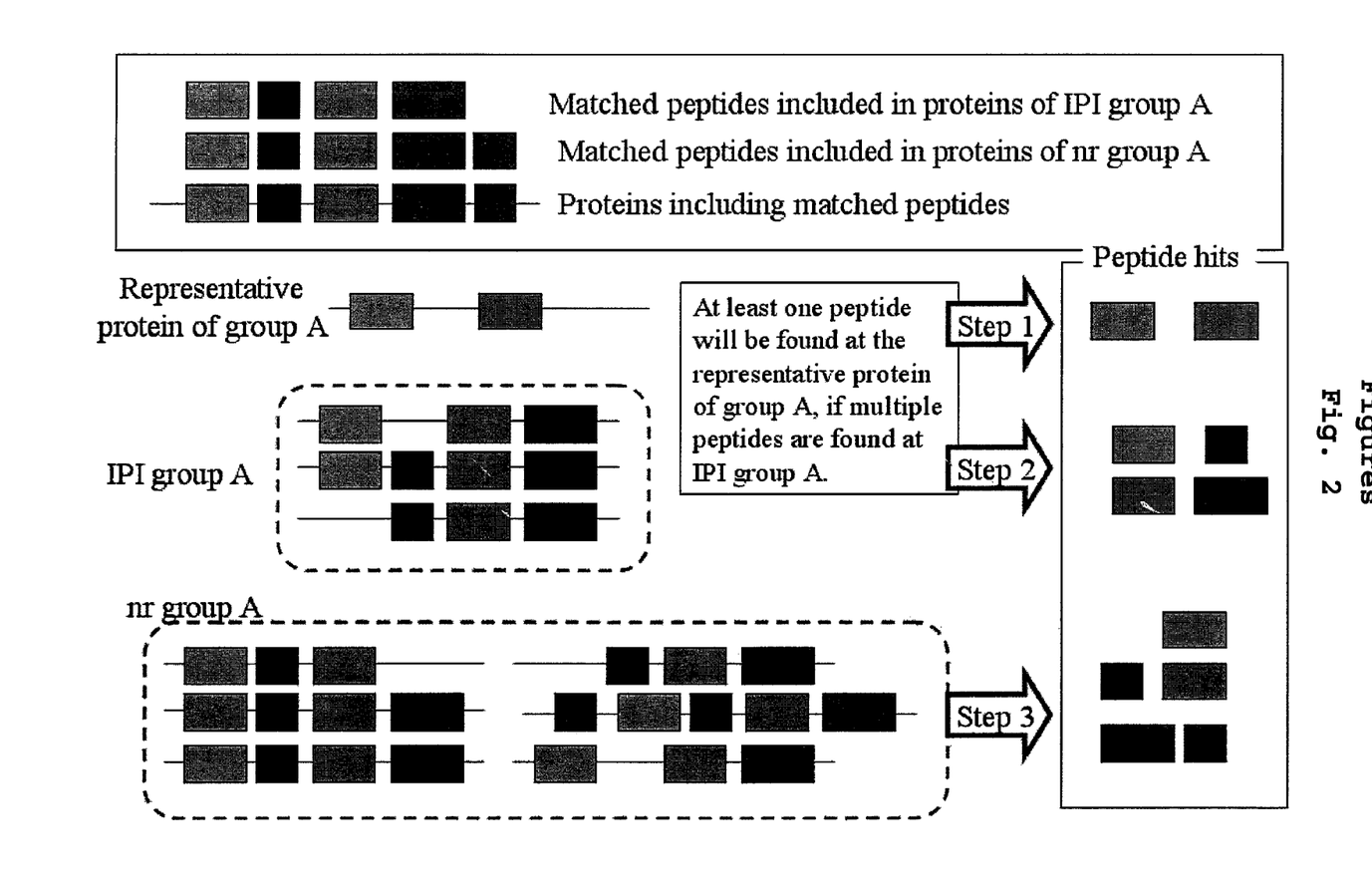
FIG. 2 is a schematic diagram illustrating the identifying procedure of peptide sequences in the same protein group by the method of the present invention.
Figure 3:
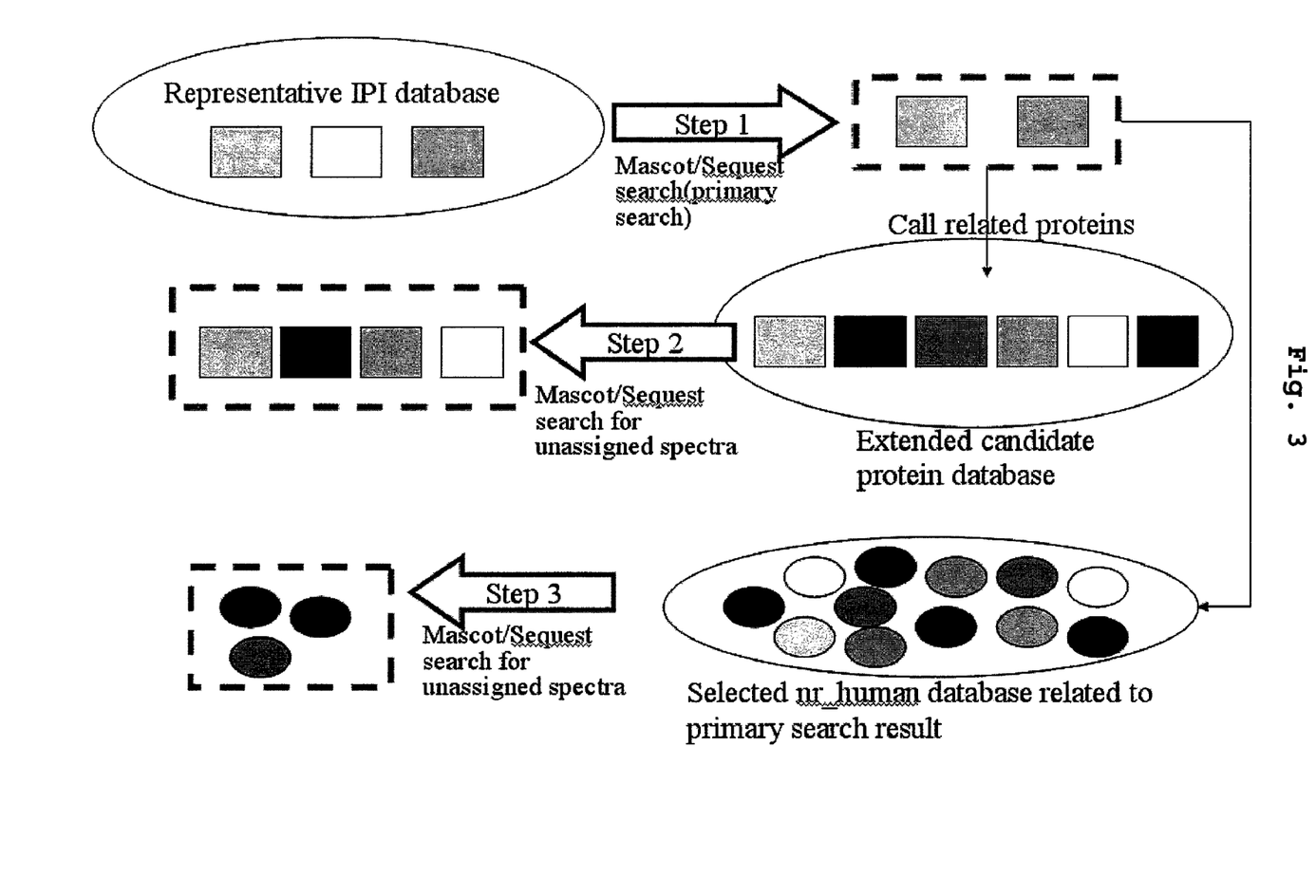
FIG. 3 is a schematic diagram illustrating the relation among proteins independently identified in each step from the above database system.

The third database is originated from another sequence database different from the database imported for generating primary and secondary database. The third database is constructed with protein groups similar to the representative proteins which are selected from the representative database. The third database is very useful to identify a protein that cannot be identified by the representative protein database and the secondary database (see FIG. 1).

The hierarchical database structure of the present invention is characterized as follows. The representative protein database indicates the classification of proteins possibly included in a sample, and it is used for appointing a representative protein contains some of those proteins. In the meantime, the third database is the database that contains many possible sequence variations of each protein group, which means protein diversity.

The mass spectrometer is a very important tool for the accurate analysis of proteins, with which the molecular weights of peptides obtained from the hydrolysis of proteins are measured and the molecular weights of fragment ions obtained from the fragmentation of the peptide are also measured and compared with those of possible protein sequences. To identify a protein, several peptides of a protein have to be identified for the reliability of the result. If a protein is identified by only one of peptide sequences that might be misidentified by the imperfectness of mass spectrum, the reliability of the identification of a protein through the database will be in doubt. So, only those proteins that are identified by at least two identified peptides have to be selected to increase the reliability of the result. In the present invention, representative proteins are selected at the first search. If at least two peptides of one protein are identified at the entire database search, the chance that one of these peptides might exist in its representative protein sequence will be high. The method for identifying a protein by comparing mass spectrum with the sequence of a protein has a problem that if a correct peptide sequence is not found in the database, even high quality mass spectrum is useless. Therefore, the database containing all the known protein sequences works better in the mass spectral analysis.

According to the method of the invention, the reconstructed protein database contains similar proteins to those included in the conventional database. Thus, such similar protein sequences are usually excluded from the protein database to construct the representative protein database. The mass spectral analysis based on the representative protein database results in less peptide sequences than when the entire database is used. If a protein is identified by several peptides from the original database, the protein is expected to include at least one peptide identified from the representative protein database. Proteins having peptides identified from the representative protein database are grouped. So, the reconstructed protein database includes much fewer protein sequences but has more peptide matches than the representative protein database. The reconstructed protein database enables to find additional peptide matches which cannot be found in the representative protein database. The proteins identified in the representative protein database can also be identified by screening the larger database such as NCBI nr database integrated from several other databases. The result of screening in larger database using only the protein groups related to the identified representative proteins is consistent with the results of screening using its whole database. However, the screening time is much shorter with the selected protein groups.

The screening without the representative protein database takes much longer time and its reliability is also in doubt. However, after grasping the possible protein groups by screening with the representative protein database, the screening takes shorter time and the results is more reliable. Furthermore, more reliable modification can be found among various sequences.

If peptide sequences are identified from the first screening of the representative protein database, peptides of the target protein can be more easily analyzed by the above protein grouping and the second screening from its related protein groups.

The present invention further provides a method for screening a protein by using the reconstructed protein database.

The present invention provides a protein screening method in bottom-up proteomics as follows:

i) A protein is obtained from a biomaterial and then hydrolyzed by a protease. The resultant peptide solution is separated into fractions by chromatography and tandem mass analysis to produce tandem mass spectra. The obtained mass spectra are transferred to a computer system for protein screening;

ii) The transmitted tandem mass spectra are screened by the newly constructed representative protein database by using algorithm for general protein screening, followed by preparing the list of primary proteins identified. The identified sequences are input in a recording system of a computer;

iii) The remaining tandem mass spectra which have not been identified in the above step ii) are screened by using the constructed secondary protein database by using algorithm for general protein screening, then the identified second protein list is prepared. The identified sequence information is recorded on a recording system of a computer;

iv) The remaining tandem mass spectrum which has not been identified from the screening of steps ii and iii is screened again by using the constructed forth protein database, and the list of identified third proteins is prepared. The identified sequence information is recorded on a recording system of a computer; and v) By combining all the lists from the primary to the third protein list, a list containing the entire identified proteins is prepared and the screening results are output through the output unit of a computer.

The protein screening method of the present invention can further include the additional steps as follows:

vi) The modified peptide sequence is screened through the constructed forth protein database by using algorithm for general protein screening and then the list of the identified forth proteins is prepared. The identified sequence information is recorded on a recording system of a computer; and vii) By combining all the lists from the primary to the forth protein list, a list containing the entire identified proteins is prepared and the screening results are output through the output unit of a computer.

In step i, the data transfer of the tandem mass spectra is performed by various buses such as RS-232C serial bus, parallel bus, universal serial bus (USB), IEEE1394, and Bluetooth, or by the steps of recording the spectra on the recorder equipped in the mass spectrometer; transferring the recorded spectrum to the mobile recoding medium such as USB memory, CD-ROM, magnetic tape, external hard disc drive, etc; and transferring the results once again to the computer for protein screening.

In steps ii~iv, the algorithm for protein screening is MOWSE algorithm (Pappin et al., *Curr. Biol.* 3:327-332, 1993) or SEQUEST algorithm (Eng et al., *J. Am. Soc. Mass Spectrom.* 5:976-989, 1994), but not always limited thereto.

In steps ii, iv and vi, various internal/external recording media can be used as a recording system of a computer, which is exemplified by HDD, FDD, CD-ROM, CD-R, CD-RW, DVD-ROM, DVD-RAM, DVD-RW±, MD (MiniDisk), MMC (MultiMedia Card), SMC (Smart Media Card), Flash-memory, SD (Secure Didital) card, CF (CompactFlash) card, MemoryStick, magnetic tape, etc, but not always limited thereto, and HDD is most preferred.

The present invention also provides a protein screening method in top-down proteomics as follows:

i) Tandem mass spectra are obtained by FT-ICR mass spectrometer from an authentic protein which has not been treated with a protease. The tandem mass spectrum is then transmitted to the computer system for protein screening;

ii) The sequence tag is searched in the constructed representative protein database to extract a protein group that is able to be identified by some of its peptides;

iii) Proteins which are similar to the representative protein found from sequence tag method are selected from the extracted protein group of step ii), leading to the preparation of the primary protein list and the construction of the second protein database;

iv) If a protein in the secondary protein database is identified by using algorithm for general protein screening, this protein is selected to construct the secondary protein list. And the identified sequence information is recorded on a recording system of a computer;

v) The protein groups of the third protein database are selected to construct the forth protein database, if they are related to the representative proteins matching with sequence tag;

vi) If a protein in the forth protein database is identified by using algorithm for general protein screening, this protein is selected to construct the third protein list. And the identified sequence information is recorded on a recording system of a computer; and vii) By combining all the lists from the primary to the third protein list, a list containing the entire identified proteins is prepared and the screening results are output through the output unit of a computer.

In step i, the data transfer of the tandem mass spectrum is performed by various buses such as RS-232C serial bus, parallel bus, universal serial bus (USB), IEEE1394 and Bluetooth, or by the steps of recording the spectrum on the recorder equipped in the mass spectrometer; transferring the recorded spectrum to the mobile recoding medium such as USB memory, CD-ROM, magnetic tape, external hard disc drive, etc; and transferring the results once again to the computer for protein screening.

In steps iv ~vi, the algorithm for protein screening is Sequence Tag algorithm (Mann M., Wilm M., *Anal. Chem.* 66(24):4390-4399, 1994), ProSightPTM algorithm (LeDuc et al., *Nucleic Acids Res.* 32: W340-345, 2004; Taylor et al., Anal. Chem., 75(16):4081-4086, 2003) or Mascot algorithm (Perkins et al., *Electrophoresis*, 20:3551-3567, 1999; Matrix Science Ltd., USA, www<dot>matrixscience<dot>com/), but not always limited thereto.

In steps iv and vi, various internal/external recording media can be used as a recording system of a computer, which is exemplified by HDD, FDD, CD-ROM, CD-R, CD-RW, DVD-ROM, DVD-RAM, DVD-RW±, MD (MiniDisk), MMC (MultiMedia Card), SMC (Smart Media Card), Flash-memory, SD (Secure Didital) card, CF (CompactFlash) card, MemoryStick, magnetic tape, etc, but not always limited thereto, and HDD is most preferred.

The present invention further provides a computer system for protein screening.

The computer system for protein screening of the present invention is composed of the input unit for inputting tandem mass spectrum; the primary protein database with a little sequence overlapping; the recording system for storing the third protein database with huge sequence overlapping; the arithmetic unit for performing computations including the first grouping computation for extracting the representative protein database from the primary protein database, the first screening computation for screening the inputted tandem mass spectrum from the representative protein database, the second grouping computation for constructing the secondary protein database comprising protein groups selected from the primary protein database, the second screening computation for screening the inputted tandem mass spectrum from the secondary database, the third grouping computation for constructing the forth protein database comprising the protein groups selected from the third database containing a variety of protein sequences, and the third screening computation for screening the inputted tandem mass spectrum from the forth protein database; and the output unit for outputting the results of the first~third screening computation.

The present invention also provides a recording medium on which the software realizing the protein screening method of the present invention is stored.

The software can be prepared by various programming languages such as C, C+, C++, Visual C, Cobol, Fotran, Basic, Q-Basic, JAVA, Perl, etc. The software of the present invention can be anyone that is able to be programmed by those in the art and there is no need to ask the program list, as long as the technical merits and algorithm realizing the embodiment of the invention are clear therein.

Advantageous Effects

The method for reconstructing protein database for identifying proteins and the method for screening a protein using the same result in the shorter screening time than the conventional protein screening method but the screening results are equal to those from the conventional method. Thus, the methods of the present invention can be effectively used for the fast and easy qualitative/quantitative analysis of a biological protein, for the development of diagnostic and therapeutic agents for various diseases and accordingly for studies on the interaction among proteins and in vivo metabolism.

DESCRIPTION OF DRAWINGS

The application of the preferred embodiments of the present invention is best understood with reference to the accompanying drawings, wherein.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Separation of Peptides from Human Serum Samples and Obtainment of Tandem Mass Spectra Thereby Human serum samples were hydrolyzed by trypsin, after one-dimensional electrophoresis to obtain one-dimensional gel. As described by Pieper et al, peptides were separated from each band by Multidimensional Protein Identification Technology (MudPIT) (Pieper, R., et al., *Proteomics*, 3: 422-432, 2003). Each band of the one-dimensional gel was cut and hydrolyzed, resulting in a peptide mixture. The peptide mixture was applied to micro-capillary column filled with C18, SCX cation exchange materials and accordingly tandem mass spectra were obtained by using mass spectrometer (LTQ/XL Linear Ion Trap Mass Spectrometer, Thermo Electron Corp., USA).

EXAMPLE 2

Results from the Conventional Protein Screening Algorithm

The tandem mass spectrum obtained in the above Example 1 was screened with the software for protein identification (TurboSEQUESTTM of Bioworks 3.1, Thermo Electron Corp., USA) by using the human protein database IPI_Human protein sequence database version 3.15.1 (ftp<dot>ebi<dot>ac<dot>uk/pub/databases/IPI/current/) selected from IPI databases downloaded from EBI, England. As a result, 2,944 proteins were identified. For reference, the IPI_Human protein sequence database version 3.15.1 is composed of 58,099 protein sequences. To identify a protein, the peptides having Xcorr value of at least 1.9 with the charge of +1, 2.2 with the charge of +2 and 3.75 with the charge of +3 are selected. The ΔCn value is preferably more than 0.1 and the RSp value is lower than 4, which are the standards used for TurboSEQUESTTM.

EXAMPLE 3

Construction of Hierarchical Database and Identification of a Protein Using the same

<3-1>

58,099 protein sequences of IPI_Human protein sequence database were grouped by at least 60% homology by using a database clustering software (CD-HIT, bioinformatics<dot>org, Li, W. et al., *Bioinformatics* 17:282-283, 2001; Li, W. et al, *Bioinformatics* 18:77-82, 2002). A representative protein was appointed in each group and those selected representative proteins were grouped into one, leading to the construction of the representative protein database. The numbers of the proteins in the representative protein database was 24,120.

<3-2>

The software for protein identification (TurboSEQUEST™) used in Example 2 was run with the representative protein database. As a result, 2,136 proteins were identified based on the mass spectrum data in Example 2. The above result indicates that the representative proteins alone can identify 73% of total target proteins.

<3-3>

6,860 proteins which were related to those identified in Example <3-2> were found in IPI_Human database. And a new database was constructed with those protein sequences, with which the software for protein identification (TurboSEQUEST™) was executed. As a result, 2,934 proteins were identified. Compared with the results of the conventional screening in Example 2, 10 proteins were missed and among them 9 proteins were not reliable because they were identified by only one peptide and the one remaining protein was identified exceptionally by the peptide which was not included in the representative protein group.

<3-4>

A database was reconstructed with 37,927 proteins selected from the human protein database (number of proteins: 283,548) of nr database (National Center for Biotechnology Information, NCBI), which is the database having the widest overlapping, which were confirmed to be related with those identified in Example <3-2>. And the software for protein identification (TurboSEQUEST™) was executed with those selected proteins. As a result, 4,090 proteins were identified, which were 39% more proteins compared with 2,944 proteins identified by the conventional screening with IPI database. Those proteins seemed to be the same kinds of proteins as those found in the conventional IPI database but some parts of their sequences were different, suggesting that those cannot be screened by the IPI database. The identified proteins of nr database include wider sequence modification than those of IPI database, so that they can be effectively used for the further investigation on protein modification.

COMPARATIVE EXAMPLE 1

IPI Human Database and NCBI nr Database Screening

A protein is identified by peptide sequences identified by screening a database. By the conventional screening on IPI database, 6,124 peptides were identified, while 6,580 peptides were identified by NCBI nr database screening (356 peptides were additionally identified). When tandem mass spectrum is screened on NCBI nr database, approximately 280,000 protein sequences have to be screened in general. However, when it is screened on the stratificational database of the invention, only 32,916 peptide sequences are required to obtain additional peptide sequences. In the meantime, the screening time of the stratificational database of the present invention is reduced by ⅓, compared with when NCBI nr database screening.

INDUSTRIAL APPLICABILITY

The method for reconstructing protein database for protein identification of the present invention and the screening method for a protein using the same can be effectively used for the fast and accurate qualitative/quantitative analysis of a biological protein and further applicable to the development of diagnostic and therapeutic agents for various diseases.

Those skilled in the art will appreciate that the conceptions and specific embodiments, disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for screening a protein comprising:
   i) grouping proteins having a required homology from a primary database by using clustering software which minimizes overlapping of proteins, thereby generating one or more protein groups, and then recording sequence information of each protein group on a recording system of a computer;
   ii) designating a representative protein in each protein group and then constructing a representative protein database composed of the representative proteins, followed by recording the representative protein database and sequence information of the representative proteins on a recording system of a computer;
   iii) screening tandem mass spectra of one or more protein samples obtained by a mass spectrometer, using sequence searching software with the representative protein database, and then preparing a primary protein list comprising representative proteins from the representative database identified by the sequence searching software as matching the one or more protein samples;
   iv) constructing a secondary protein database comprising proteins from each protein group having a representative protein from the primary protein list, and then recording the secondary protein database and sequence information of the secondary database proteins on a recording system of a computer;
   v) screening tandem mass spectra of each protein sample obtained by the mass spectrometer using sequence searching software with the secondary protein database and then preparing a secondary protein list comprising proteins from the secondary protein database identified by the sequence searching software as matching the one or more protein samples;
   vi) selecting protein isoforms of proteins from the primary protein list made in the above step iii) from a third database containing various isoforms of protein sequences and then grouping the selected proteins to construct a fourth protein database, followed by recording the fourth protein database and sequence information of the fourth database proteins on a recording system of a computer;
   vii) screening tandem mass spectra of a specific sample obtained by a mass spectrometer using sequence searching software with the fourth protein database and then preparing a third protein list comprising proteins from the fourth protein database identified by the sequence searching software as matching the specific sample;
   viii) screening tandem mass spectra of the specific sample obtained by the mass spectrometer using sequence searching software containing modification conditions with the fourth protein database and then preparing a fourth protein list comprising modified proteins from the fourth protein database identified by the sequence searching software as matching the specific sample; and
   ix) preparing a list of identified proteins comprising all the proteins from the primary protein list, secondary protein list, third protein list and fourth protein list, and printing the identified protein list using an output unit of a computer.

2. The method for screening a protein according to claim 1, wherein the primary database is IPI database, UniprotKB/Swissprot database or nrdb90 database.

3. The method for screening a protein according to claim 1, wherein the clustering software is selected from a group consisting of CD-HIT, GeneRAGE, TribeMCL and nrdb90.

4. The method for screening a protein according to claim 1, wherein the homology of the protein is 60%, 65%, 70%, 75%, 80%, 85%, 90% or 95%.

5. The method for screening a protein according to claim 1, wherein the homology is 60%.

6. The method for screening a protein according to claim 1, wherein the sequence information of step ii, iv and vi is formatted by FASTA.

7. The method for screening a protein according to claim 1, wherein the recording system of a computer of step ii, iv and vi is selected from a group consisting of HDD, FDD, CD-ROM, CD-R, CD-RW, DVD-ROM, DVD-RAM, DVD-RW±, MD (MiniDisk), MMC (MultiMedia Card), SMC (Smart Media Card), Flashmemory, SD (Secure Didital) card, CF (CompactFlash) card, MemoryStick and magnetic tape.

8. The method for screening a protein according to claim 1, wherein the sequence screening software of step iii) and v) is selected from a group consisting of SEQUEST, Mascot, Sonar and X!Tandem.

9. The method for screening a protein according to claim 1, wherein the third database is NCBI nr database, EST database or a protein sequence database encoded from genomic nucleotide sequences.

10. A method for screening a protein, wherein the method comprises the following steps:
   i) obtaining a protein from a biomaterial and then hydrolyzing the protein using a protease, thereby generating a peptide solution, performing chromatography and tandem mass analysis on the generated peptide solution to obtain tandem mass spectra and transferring the obtained mass spectra to a computer system for protein screening;
   ii) screening the transferred tandem mass spectra against a constructed representative protein database using an algorithm for general protein screening, followed by preparing a list of primary proteins identified and inputting the primary list of identified proteins in a recording system of a computer;
   iii) screening remaining tandem mass spectra which have not been identified in the above step ii) against a constructed secondary protein database using an algorithm for general protein screening, preparing a second list of identified proteins and recording sequence information of the second list of identified proteins on a recording system of a computer;
   iv) selecting protein isoforms of proteins from the primary protein list made in the above step ii) from a third database containing various isoforms of protein sequences and then grouping the selected proteins to construct a fourth protein database;
   v) screening remaining tandem mass spectra which have not been identified from the screening of steps ii and iii against the fourth protein database and preparing a third list of identified proteins and recording sequence information of the third list of identified proteins on a recording system of a computer; and vi) combining the primary list, second list and third list to generate an identified protein list containing all of the identified proteins and outputting the identified protein list to an output unit of a computer.

11. The method for screening a protein according to claim 10, wherein the method additionally includes the following steps:
  vii) screening a modified peptide sequence against the constructed fourth protein database using an algorithm for general protein screening and then preparing a fourth identified protein list and recording sequence information of the fourth list of identified proteins on a recording system of a computer; and
  viii) combining the primary list, second list, third list and fourth list to generate an identified protein list containing all of the identified proteins and outputting the identified protein list to an output unit of a computer.

12. The method for screening a protein according to claim 10, wherein the transfer of the tandem mass spectra of step i is performed using a RS-232C serial bus, parallel bus, universal serial bus (USB), IEEE1394, or Bluetooth, or by the steps of recording the spectra on a recorder equipped in a mass spectrometer; transferring the recorded spectra to a mobile recording medium; and transferring the obtained mass spectra to the computer system for protein screening.

13. The method for screening a protein according to claim 10, wherein the algorithm for protein sequence screening is MOWSE algorithm or SEQUEST algorithm.

14. The method for screening a protein according to claim 10, wherein the recording system of a computer of steps ii-iv is selected from a group consisting of hard disc drive, floppy disc drive, CD-ROM, CD-R, CD-RW, DVD-ROM, DVD-RAM, DVD-RW±, MD (MiniDisk), MMC (MultiMedia Card), SMC (Smart Media Card), flash memory, SD (Secure Digital) card, CF (CompactFlash) card, memory stick and magnetic tape.

15. A method for screening a protein, which comprises the following steps:
  i) obtaining tandem mass spectra using a ft-icr mass spectrometer from intact proteins which have not been treated with a protease, and transferring the obtained tandem mass spectra to a computer system for protein screening;
  ii) searching a sequence tag in a constructed representative protein database to extract a protein group that is able to be identified by some of its peptides;
  iii) selecting proteins having a required homology to proteins in a primary protein database from the extracted protein group of step ii, thereby generating a second protein database;
  iv) identifying one or more proteins by molecular weight from the secondary protein database using an algorithm for general protein screening, thereby generating a secondary protein list, and recording sequence information of the identified proteins on a recording system of a computer;
  v) selecting proteins in a third protein database from the extracted protein group of step ii, thereby generating a fourth protein database;
  vi) identifying one or more proteins by molecular weight from the fourth protein database using an algorithm for general protein screening, thereby generating a third protein list, and recording sequence information of the identified proteins on a recording system of a computer; and
  vii) combining the primary list, secondary list and third list to generate an identified protein list containing all of the identified proteins and outputting the identified protein list to an output unit of a computer.

16. The method for screening a protein according to claim 15, wherein the transfer of the tandem mass spectra of step i is performed using a RS-232C serial bus, parallel bus, universal serial bus (USB), IEEE1394, or Bluetooth, or by the steps of recording the spectra on a recorder equipped in a mass spectrometer; transferring the recorded spectra to a mobile recording medium; and transferring the obtained mass spectra to the computer system for protein screening.

17. The method for screening a protein according to claim 15, wherein the algorithm for protein sequence screening is selected from a group consisting of Mascot algorithm, Sequence Tag algorithm and ProSightPTM algorithm.

18. The method for screening a protein according to claim 15, wherein the recording system of a computer of step iv or vi is selected from a group consisting of HDD, FDD, CD-ROM, CD-R, CD-RW, DVD-ROM, DVD-RAM, DVD-RW±, MD (MiniDisk), MMC (MultiMedia Card), SMC (Smart Media Card), flash memory, SD (Secure Digital) card, CF (CompactFlash) card, memory stick and magnetic tape.

* * * * *